United States Patent [19]

Byrom

[11] Patent Number: 5,273,891
[45] Date of Patent: * Dec. 28, 1993

[54] PROCESS FOR THE PRODUCTION OF MICROBIAL CELLULOSE

[75] Inventor: David Byrom, Middlesbrough, England

[73] Assignee: Imperial Chemical Industries PLC, London, England

[*] Notice: The portion of the term of this patent subsequent to May 29, 2090 has been disclaimed.

[21] Appl. No.: 773,997

[22] Filed: Oct. 9, 1991

Related U.S. Application Data

[63] Continuation of Ser. No. 659,468, Feb. 25, 1991, abandoned, which is a continuation of Ser. No. 293,520, Jan. 5, 1989, abandoned.

[30] Foreign Application Priority Data

Jan. 6, 1988 [GB] United Kingdom ................. 8800183

[51] Int. Cl.$^5$ .......................... C12P 19/04; C12R 1/02
[52] U.S. Cl. ..................................... 435/101; 435/823
[58] Field of Search ............................... 435/101, 823

[56] References Cited

U.S. PATENT DOCUMENTS

| | | |
|---|---|---|
| 3,223,697 | 12/1965 | Ball et al. . |
| 3,784,408 | 1/1974 | Jaffe et al. . |
| 3,808,192 | 4/1974 | Dimitri . |
| 4,378,431 | 3/1983 | Brown .................................. 435/101 |
| 4,745,058 | 5/1988 | Townsley .............................. 435/101 |
| 4,929,550 | 5/1990 | Byrom ................................... 435/101 |

FOREIGN PATENT DOCUMENTS

| | | |
|---|---|---|
| 228779 | 7/1987 | European Pat. Off. ............ 435/101 |
| 279506 | 8/1988 | European Pat. Off. . |
| 323717 | 7/1989 | European Pat. Off. . |
| 265990 | 11/1987 | Japan .................................... 435/101 |

OTHER PUBLICATIONS

Chemical Abstracts, vol. 94, No. 2, 1981, p. 221, abstract No. 7291v Columbus, Ohio, US; A. M. Prabhu et al.

*Primary Examiner*—Herbert J. Lilling
*Attorney, Agent, or Firm*—Cushman, Darby & Cushman

[57] ABSTRACT

A process for the production of extra-cellular microbial cellulose in which a novel strain of the genus Acetobacter capable of producing extra-cellular microbial cellulose is aerobically cultivated in an aqueous culture medium containing a carbon source and other necessary nutrients. The novel strain is also claimed.

9 Claims, No Drawings

PROCESS FOR THE PRODUCTION OF MICROBIAL CELLULOSE

This is a continuation of application Ser. No. 07/659,468, filed on Feb. 25, 1991, which was abandoned upon the filing hereof which was a continuation of application Ser. No. 07/293,520, filed Jan. 5, 1989, now abandoned.

This invention relates to a process for the production of microbial cellulose.

A number of bacteria, particularly strains of the genus Acetobacter, can be cultivated to produce microbial cellulose. The microbial cellulose is produced extra-cellularly in the form of a fibril attached to the bacterial cell. Fibrils from different cells intermesh to give pellicles which are mixtures of cellulose and cells.

Initially microbial cellulose was produced using static cultivation as in the process disclosed in GB 2131701. In such processes the pellicles of microbial cellulose are formed upon the surface of the static culture which is usually contained in shallow trays.

More recently however in our Published European Patent Specification No. 279506 we have proposed a process for the production of microbial cellulose which comprises the following steps:

(a) a growth step in which a suitable bacterial strain is cultivated in stirred batch culture until substantially all the carbon source present has been utilized and the culture is carbon limited;

(b) an accumulation step in which the carbon source is supplied continuously to the carbon limited culture at a rate sufficient to maintain it in carbon limitation and to enable microbial cellulose to accumulate during stirred cultivation;

(c) a removal step in which bacterial cells and accumulated microbial cellulose are removed from the culture at the end of the accumulation step; and (d) a separation step in which microbial cellulose is separated from the cells.

Microbial cellulose pellicles have excellent liquid absorbing properties and can be used in a wide variety of medical applications, eg in absorbent pads as described in GB 2131701. For such medical applications the pellicles produced in static culture can be used directly. However, there are other non-medical uses for microbial cellulose and for such non-medical uses it is generally necessary for the pellicles to be broken into smaller pieces.

Microbial cellulose can be regarded as an extra-cellular polysaccharide. Such polysaccharides when produced by batch or continuous cultivation processes are normally produced with a substantial surplus of carbon source present in the medium under conditions of limitation by another nutrient such as the nitrogen or phosphorus sources. Often the carbon source is present in very considerable excess eg in processes for producing xanthan gums.

A number of bacterial strains have been reported which can produce extra-cellular microbial cellulose including for example strains of the species *Acetobacter xylinum*, such as strain ATCC 23769, and strains of *Acetobacter aceti*, such as subsp. orleanensis strain NCIB 8747. However if microbial cellulose is to be produced successfully on a commercial scale it is important that bacterial strains having improved ability to be cultivated to produce microbial cellulose are developed.

According to the present invention we provide a process for the production of extra-cellular microbial cellulose in which a bacterial strain capable of producing extra-cellular microbial cellulose is aerobically cultivated in an aqueous culture medium containing a carbon source and other necessary nutrients wherein the bacterial strain is Acetobacter sp strain NCIB 12548 or a variant or mutant strain derived therefrom.

Also according to the invention we provide a biologically pure culture of Acetobacter sp strain NCIB 12548 or a variant or mutant derived therefrom.

Acetobacter sp strain NCIB 12548 (also designated by us as strain 99) was received and accepted for deposit on Sep. 24, 1987, under the terms of the Budapest Treaty on the International Recognition of the deposit of microorganisms for the purposes of patent procedure, by the National Collections of Industrial and Marine Bacteria (NCIMB), PO Box No. 31, 135 Abbey Road, Aberdeen, AB9 8DG, Scotland, UK.

In the process of the invention the carbon source is suitably a carbon source for growth but this is not necessarily the case. A wide range of carbon sources may be used including lactate, ethanol, glycerol, molasses and other sugars such as fructose and particularly glucose.

Suitably microbial cellulose can be produced by growing Acetobacter sp NCIB 12548 by the process of our Published European Patent Specification No. 279506 having the steps (a) to (d) described above. In this process suitably the culture medium for the growth step initially contains the carbon source at a concentration within the range 2 to 20 g/l. During the accumulation step the carbon source is preferably supplied to the culture at a concentration within the range 1 to 10 g/l per hour. A suitable culture medium for the growth and accumulation steps has the following composition:

| | |
|---|---|
| Peptone ('oxoid') | 5.0 g/l |
| Yeast extract ('oxoid') | 5.0 g/l |
| Na$_2$HPO$_4$ | 2.7 g/l |
| Citric acid | 1.15 g/l |
| Glucose | 20 g/l |
| Made up to pH 6.0 | |

The initial pH at which the growth and accumulation steps are carried out is suitably within the range 4 to 6.5 with a pH of approximately 5 being preferred. Suitably the growth and accumulation steps are carried out at a temperature within the range 15° C. to 35° C., preferably within the range 20° C. to 28° C.

During the accumulation step the culture is supplied with the carbon source at a rate such that the level of this source in the supernatant liquid is maintained within the range 0 to 0.5 g/l. Concentrations of other nutrients in the culture are gradually reduced until the supply of one or more of the other nutrients in the culture becomes exhausted. The accumulation step can be terminated at this point or further supplies of the other nutrients can be added. In the latter case cultivation can be continued until the culture becomes too viscous for satisfactory aeration. During the accumulation step extra-cellular microbial cellulose is formed as flocs rather than the large pellicles formed during static cultivation.

After completion of the accumulation step, the mass of cells and accumulated microbial cellulose is removed from the culture in the removal step by any suitable method. Preferably, this is done by filtration. The cellulose is thereafter separated from the cells in the separation step. The separation is suitably done by treating the mass of cellulose and cells-with a reagent, eg an alkaline reagent, which will dissolve the cells without affecting the cellulose which can then be separated. A preferred method for dissolving the cells and separating the cellulose is to treat the cell/cellulose mass with a dilute sodium hydroxide solution, e.g. a 0.1–5.0% (preferably 0.3–3%) sodium hydroxide solution. After separation the microbial cellulose can be further treated, e.g. by drying.

When the process of the invention is carried out in the manner described in Published European Patent Specification No. 279506 the growth and accumulation steps can be preferably carried out in the same fermenter. They can, however, be carried out in separate fermenters with the culture produced in the growth step being transferred from the fermenter in which it is produced into a second fermenter to which the carbon source is supplied continuously. This transfer can be ma.. before the growth step is completed and before growth under carbon limitation has begun. The fermenters used can be stirred mechanically or can be of the "air-lift" type in which stirring is effected by blowing an oxygen-containing gas into the fermenter.

Examples of suitable "air-lift" fermenters are those described in our Patent Specifications Nos. GB 1353008, 1417486 and 1417487.

The process of the invention can also be carried out in static or in continuous culture. In static culture the bacterium is suitably cultured in a liquid nutrient medium at an initial pH within the range 4 to 6.5 (preferably approximately 5) and at a temperature within the range 15° to 35° C., most preferably 20° to 28° C. In order to obtain the coherent gel-like material useful for a wound dressing or other medical applications, it is important that the culturing medium remain substantially motionless during the culturing period which may be from a matter of a few hours for a thin membrane of 0.1 millimeter thickness to several days or weeks for a pellicle having a thickness of 15 millimeters or greater. In static culture the bacterium is cultured at the surface of a nutrient medium to form a coherent pellicle. This pellicle is removed from the-nutrient, treated with sodium hydroxide or other agent to remove the bacterium, neutralised, and washed with water to obtain a water-loaded pellicle of microbial cellulose. The pellicle thus formed may be cut to any desired size, sterilized by heat or irradiation and used for example as a dressing for burns or other skin injury. In another use, the water may be exchanged with glycerol or other physiologically compatible liquid, and/or medicaments may be incorporated prior to sterilization and use. The liquid-loaded pellicle can be packaged in a sterile, moisture-impervious container for long-term storage.

The microbial cellulose produced by a process having steps (a) to (d) above (particularly using the process of the invention) is more readily usable as a bulking agent in foods or as a tabletting aid than is the microbial cellulose produced in pellicle form by static cultivation processes.

The invention is illustrated by the following example:

EXAMPLE

A shake flask was inoculated with strain NCIB 12548 (otherwise known as strain 99) which was grown for 24 hours after which time the purity of the resulting cellulose was assessed. This culture was then transferred to a fermenter containing a medium in which the carbon source glucose was present at a concentration of 10 g/l. The glucose concentration was monitored during growth of the culture and, when it was found to have fallen to 0.5 g/l, feeding of glucose to the fermenter was begun and was continued for 64 hours. Measurements of cell dry weight (g/l), cellulose dry weight (g/l) and glucose uptake (g/l) were taken at intervals and the results are set out in the Table. This shows that the optimum yield of cellulose (i.e. g cellulose per g glucose) was achieved after 41 h. Thereafter glucose continued to be consumed to produce increased cell dry weight for approximately a further 7 hours without producing further cellulose.

TABLE

| Fermentation time (h) | Dry cell weight (g/l) | Cellulose weight dry (g/l) | Glucose uptake (g/l) | Cellulose yield (g cell/g glucose) |
|---|---|---|---|---|
| 16.5 | 1.38 | 0.29 | 11.15 | 0.026 |
| 23.0 | 4.8 | 1.54 | 13.62 | 0.113 |
| 41.0 | 6.3 | 4.50 | 23.80 | 0.189 |
| 48 | 9.3 | 4.40 | 28.95 | 0.152 |
| 64.0 | 9.2 | 4.50 | 37.82 | 0.119 |

I claim:

1. A process for the production of microbial cellulose which comprises
   supplying a carbon source continuously to a culture of Acetobacter at a rate sufficient to maintain a concentration of the carbon source of at most 0.5 g/l in the liquid phase, and
   stirring the culture so as to enable microbial cellulose to accumulate in substantially non-pellicular form.

2. A process according to claim 1 wherein the carbon source is a carbon source for growth.

3. A process according to claim 2 wherein the carbon source is glucose.

4. A process according to claim 1 which comprises the following steps:
   (a) a growth step in which a suitable bacterial strain is cultivated in stirred batch culture until substantially all the carbon source present has been utilized and the culture is carbon limited;
   (b) an accumulation step in which the carbon source is supplied continuously to the carbon limited culture at a rate sufficient to maintain it in carbon limitation and to enable microbial cellulose to accumulate during stirred cultivation;
   (c) a removal step in which bacterial cells and accumulated microbial cellulose are removed from the culture at the end of the accumulation step; and
   (d) a separation step in which microbial cellulose is separated from the cells.

5. A process according to claim 4 wherein the initial pH at which the growth and accumulation steps are carried out is within the range 4 to 6.5.

6. A process according to claim 4 wherein the growth and accumulation steps are carried out at a temperature within the range 20° to 28° C.

7. A process according to claim 4 wherein during the accumulation step the culture is supplied with the carbon source at a rate such that the level of this source in the supernatant liquid is maintained within the range 0 to 0.5 g/l.

8. A process according to claim 4 wherein during the accumulation step the concentrations of nutrients other than the carbon source in the culture are reduced until the supply of one of these other nutrients in the culture becomes exhausted.

9. A process according to claim 1 which is carried out in static culture at an initial pH within the range 4 to 6.5 and at a temperature within the range 15° to 35° C.

* * * * *